US012693363B2

(12) United States Patent
Jung et al.

(10) Patent No.: US 12,693,363 B2
(45) Date of Patent: Jul. 28, 2026

(54) METHOD AND APPARATUS FOR EVALUATING SUBJECT WITH EXCITATION TIME MAP

(71) Applicant: POSTECH RESEARCH AND BUSINESS DEVELOPMENT FOUNDATION, Pohang-si (KR)

(72) Inventors: Jae-Hun Jung, Pohang-si (KR); Se Hun Chun, Seoul (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 502 days.

(21) Appl. No.: 18/077,628

(22) Filed: Dec. 8, 2022

(65) Prior Publication Data

US 2023/0204699 A1     Jun. 29, 2023

(30) Foreign Application Priority Data

Dec. 10, 2021    (KR) ........................ 10-2021-0176724

(51) Int. Cl.
*G01R 33/56* (2006.01)
*A61B 5/055* (2006.01)
(Continued)

(52) U.S. Cl.
CPC .......... *G01R 33/5608* (2013.01); *A61B 5/055* (2013.01); *G06T 11/26* (2026.01); *G06T 2210/41* (2013.01)

(58) Field of Classification Search
CPC .......... G01R 33/5608; G01R 33/56341; A61B 5/055; A61B 5/7264; A61B 5/367;
(Continued)

(56) References Cited

U.S. PATENT DOCUMENTS

| | | | |
|---|---|---|---|
| 10,354,758 B2 * | 7/2019 | Yang ...................... | G16H 50/50 |
| 2006/0229856 A1 * | 10/2006 | Burrus ................... | G16H 30/40 |
| | | | 703/11 |

(Continued)

FOREIGN PATENT DOCUMENTS

| | | | | |
|---|---|---|---|---|
| CN | 113361688 A | * | 9/2021 | ............. G06N 3/045 |
| DE | 10112096 A1 | * | 9/2002 | ........... G06T 7/0012 |
| KR | 101741580 B1 | * | 5/2017 | ............. G16H 50/50 |

OTHER PUBLICATIONS

Basser et al "In Vivo fiber Tractography Using DT-MRI Data" Magnetic Resonance in Medicine, 44:625-63 (2000 (Year: 2000).*
(Continued)

*Primary Examiner* — Eman A Alkafawi
*Assistant Examiner* — Dilara Sultana
(74) *Attorney, Agent, or Firm* — Morgan, Lewis & Bockius LLP

(57) ABSTRACT

There is provided an analysis device for generating an excitation time map, which includes an interface device configured to receive time-series medical images of a subject and a computing device configured to generate an excitation time map by solving a diffusion reaction of electrical signals calculated from the time-series medical images using a solution of an ordinary differential equation. The excitation time map indicates excitation times at grid points of the time-series medical image.

8 Claims, 8 Drawing Sheets

(51) Int. Cl.
G06T 11/20 (2026.01)
G06T 11/26 (2026.01)

(58) Field of Classification Search
CPC ..... A61B 5/7282; A61B 5/0033; A61B 5/346;
A61B 5/372; A61B 5/4064; A61B
5/7275; G06T 11/206; G06T 2210/41;
G16H 30/20; G16H 30/40; G16H 50/20
See application file for complete search history.

(56) References Cited

U.S. PATENT DOCUMENTS

| | | | | |
|---|---|---|---|---|
| 2011/0262021 A1* | 10/2011 | Liu | ..................... | A61B 5/0042 |
| | | | | 324/309 |
| 2013/0226542 A1* | 8/2013 | Rapaka | ................... | G06T 7/149 |
| | | | | 703/2 |
| 2017/0068796 A1* | 3/2017 | Passerini | ................. | G06F 30/20 |
| 2019/0076041 A1* | 3/2019 | Ashihara | ................ | A61B 5/743 |

OTHER PUBLICATIONS

Krishnamoorthi et al. "Simulation Methods and Validation Criteria for Modeling Cardiac Ventricular Electrophysiology", PLoS One. Dec. 10, 2014;9(12): (Year: 2014).*

R. L. Winslow et al., "Mapping, modeling, and visual exploration of structure-function relationships in the heart," in IBM Systems Journal, vol. 40, No. 2, pp. 342-359, 2001. (Year: 2001).*

A. Yang et al. "A composite visualization method for electrophysiology-morphous merging of human heart", BioMed Eng. OnLine (2017) 16:70 (Year: 2017).*

B. Cantwell et al. "Techniques for automated local activation time annotation and conduction velocity estimation in cardiac mapping" , Computers in Biology and Medicine 65 (2015) 229-242. (Year: 2015).*

* cited by examiner

ANALYSIS DEVICE

200

| STORAGE DEVICE (210) | INTERFACE DEVICE (240) |
| MEMORY (220) | COMMUNICATION DEVICE (250) |
| COMPUTING DEVICE (230) | OUTPUT DEVICE (260) |

METHOD AND APPARATUS FOR EVALUATING SUBJECT WITH EXCITATION TIME MAP

CROSS-REFERENCE TO RELATED APPLICATION

This application claims priority to and the benefit of Korean Patent Application No. 10-2021-0176724, filed on Dec. 10, 2021, the disclosure of which is incorporated herein by reference in its entirety.

BACKGROUND

1. Field

The following description relates to a technique for analyzing the propagation of biological signals.

2. Discussion of Related Art

Biological signals are used to evaluate a person's condition or disease. Biological signals include electrical signals from the heart, spikes in nerve fibers, and the like.

Biological signal simulation is used to analyze biological signals. The shape of a heart or brain may be obtained through magnetic resonance imaging (MRI) or diffusion tensor imaging (DTI). The shape of the heart or brain is approximately expressed as a triangular or quadrangular three-dimensional mesh through grid-generating software that processes MRI images or DTI images. The propagation of biological signals is simulated by solving a set of partial differential equations (PDEs) on a multidimensional mesh representing specific tissue.

Generally, a mesh contains hundreds of thousands to millions of elements. Meanwhile, it may take several days or weeks to calculate PDEs for a large number of elements depending on the number of variables or the number of ion channels considered. In particular, in biological signal simulation, the propagation of electrical signals corresponding to information transfer between cells or modeling of action potentials is the most time-consuming.

There have been conventional studies for reducing time required for modeling of information transfer between cells. However, it is still challenging to simulate the propagation of biological signals within a clinically meaningful computational time in conventional studies.

SUMMARY

The following description can provide a new technique for simulating the propagation of biological signals within a relatively short computational time. The following description can also provide a tool for analyzing current propagation using a map representing the excitation of cells during a specific period.

In one general aspect, there is provided an analysis device for generating an excitation time map, including an interface device configured to receive time-series medical images of a subject and a computing device configured to generate an excitation time map by solving a diffusion reaction of electrical signals calculated from the time-series medical images using a solution of an ordinary differential equation. The excitation time map indicates excitation times at grid points of the time-series medical image.

In another general aspect, there is provided a method of evaluating a subject using an excitation time map, including receiving, by an analysis device, time-series medical images of a subject, generating, by the analysis device, an excitation time map by solving a diffusion reaction of electrical signals calculated from the time-series medical images using a solution of an ordinary differential equation, and comparing, by the analysis device, the excitation time map for the subject with a pre-built reference excitation time map and evaluating a condition of the subject.

DETAILED DESCRIPTION

Figure 1:
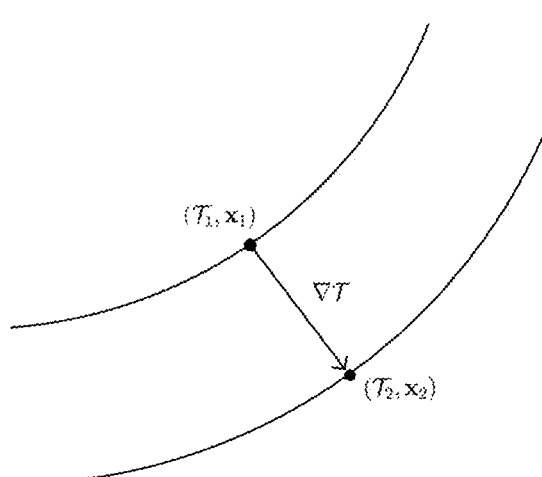
FIG. 1 illustrates an example of a gradient of an excitation time map.

While the following description may have various modifications and alternative forms, specific embodiments are shown by example in the accompanying drawings and will be described herein in detail. However, it should be understood that there is no intent to limit the present invention to the particular forms disclosed. On the contrary, the present invention is to cover all modifications, equivalents, and alternatives falling within the spirit and scope of the present invention.

It will be understood that although the terms "first," "second," etc., may be used herein to describe various elements, these elements should not be limited by these terms. These terms are only used to distinguish one element from another element. For example, a first element could be called a second element, and similarly, a second element could be called a first element, without departing from the scope of the present invention. As used herein, the term "and/or" includes any and all combinations of one or more of the associated listed items.

In terms used herein, the singular forms "a" and "an" are intended to also include the plural forms, unless the context clearly indicates otherwise. It should be further understood that the terms "comprise," "comprising," "include," and/or "including," when used herein, specify the presence of stated features, numbers, steps, operations, elements, parts, or combinations thereof, but do not preclude the presence or addition of one or more other features, numbers, steps, operations, elements, parts, or combinations thereof.

Prior to the detailed description of the drawings, it is intended to clarify that components in this specification are merely classified for each main function that each component is responsible for. That is, two or more components to be described below may be combined into one component, or one component may be divided into two or more components for each performing a subdivided function. In addition, each of the components to be described below may additionally perform some or all of the functions of other components in addition to the main functions it is responsible for, and some of the main functions that each of the components is responsible for may be exclusively performed by other components.

In addition, in performing a method or operation method, processes constituting the method may be performed differently from the specified order unless the context clearly indicates a specific order. That is, processes may be performed in the same order as specified, may be performed substantially concurrently, or may be performed in reverse order.

The following description relates to a technique for analyzing the electrical signals of a specific biological tissue. Here, the biological tissue may include the brain, heart, and the like. The activity of specific biological tissue may be defined as the propagation of electrical signals between cells.

As described above, in biological signal simulation, the propagation of electrical signals between cells or modeling of action potentials is the most time-consuming. The propagation of the electrical signal is represented by the Laplacian operator. In contrast, a reaction function is only responsible for the local approximation of ion channels at a corresponding point, and thus less resources are consumed regardless of the amount of time. In the following description, the Laplacian operator is replaced with a map representing the excitation of cells. Hereinafter, the map representing the excitation of cells is referred to as a time map or an excitation time map (ETM). Therefore, the present invention uses an ordinary differential equation (ODE) consisting only of a reaction function to describe the mechanism of an ion channel. In other words, the present invention uses an ETM over a time-dependent multidimensional domain to solve the ODE.

The present invention may be used for various biological signal analyses. However, for convenience of description, electrical signals of heart tissue will be mainly described below.

The dynamics of the diffusion-reaction mechanism may be described as follows. A governing equation may be expressed as Equation 1 below using a partial differential equation on a one-dimensional isotropic line.

$$\frac{\partial u}{\partial t} = \frac{\partial^2 u}{\partial x^2} + R(u, \ldots) \qquad \text{[Equation 1]}$$

R(u, . . . ) denotes a reaction function for a membrane potential u and other ion channel parameters. It is assumed that cell A and cell B are in close proximity. When cell A has a maximum membrane potential at a time $T_A$, $T_A$ denotes an excitation time for cell A. Cell B maintains a resting potential or a zero potential.

Cell A and cell B are close enough to transmit information. Therefore, some membrane potential in cell A is transferred to cell B through dynamic transport such as diffusion. When cell B receives a sufficient membrane potential exceeding a threshold value, some ion channels are excited to increase the membrane potential further. $T_B$ denotes a period of time for cell B to reach a maximum membrane potential. In this case, in $x_B$, Equation 1 may be replaced with an ODE such as Equation 2 below.

$$\frac{du(x_B)}{dt} = I_{app}\delta_T^{T_B} + R(u(x_B), \ldots) \qquad \text{[Equation 2]}$$

$$\delta_B^A$$

denotes a Kronecker delta function, and is 1 when A=B and 0 otherwise. A constant $I_{app}$ denotes the magnitude of current externally applied to cell B. $I_{app}$ is equal to a membrane potential transferred from cell A to cell B in the period of time $T_B$.

Meanwhile, changes in $I_{app}$ are often observed in heart tissue with various types and shapes. Therefore, in the present invention, a variable $I_{app}$ may be used for higher accuracy. However, in the following description, a constant $I_{app}$ is used for a simple description. Even when a constant value is used, accuracy is not significantly degraded.

An ETM $\mathcal{T}$ is a scalar map representing excitation times at grid points of all domains of Equation 2 equivalent to Equation 1.

The ETM $\mathcal{T}$ denotes the time when a wavefront of a wavelength passes through a point $x_i$. In this case, the time may be calculated by solving the partial differential equation of Equation 1 on a given domain $\Omega$.

A wavefront of a propagated excitation wave, which satisfies du/dt>0 is positioned at a weighted sum of a gradient of the membrane potential u over a time $t_j$. Therefore, the ETM is defined as the below equation, such as $\mathcal{T}$ : $\mathbb{R}^n \rightarrow \mathbb{R}$ using a vector for a scalar map.

$$\mathcal{T}(x_i) = \frac{\sum_j t_j \|\nabla u(x_i, t_j)\|}{\sum_j \|\nabla u(x_i, t_j)\|} - T_0, \qquad \text{[Equation 3]}$$

$$\text{for all } t = t_j \text{ satisfying } \frac{du}{dt} > C$$

$T_0$ denotes an excitation delay of an ion channel reaction with respect to the position of the wavefront calculated in Equation 3. Alternatively, it is also possible to use the following expression.

$$\mathcal{T}(x_i) = \frac{\sum_j t_j du^+/dt(x_i, t_j)}{\sum_j \|du^+/dt(x_i, t_j)\|} = \frac{\int t(du^+/dt)dt}{\int (du^+/dt)dt} \qquad \text{[Equation 4]}$$

du*/dt is defined as in Equation 5 below.

$$\frac{du^+}{dt} = \text{maxmod}\left\{\frac{du}{dt}, 0\right\} \qquad \text{[Equation 5]}$$

For each integral, the following operations are used in the derivative (differentiation).

$$\int \frac{du^+}{dt} dt = u(t_1^+) - u(t_0^+),$$

-continued $$\int t \frac{du^+}{dt} dt = tu\big|_{t_0^+}^{t_1^+} - \int_{t_0^+}^{t_2^+} u\,dt$$

When du/dt has a positive value, $$t_0^+ \text{ and } t_1^+$$

denote a first time and a final time, respectively. In this case, Equation 4 may be expressed as Equation 6 below.

$$\mathcal{T}(x_i) = \frac{1}{u(t_1^+) - u(t_0^+)} \left[ t_1^+ u(t_1^+) - t_0^+ u(t_0^+) - \int_{t_0^+}^{t_1^+} u\,dt \right] \qquad \text{[Equation 6]}$$

The excitation of the reaction function R(u, . . . ) may be an exponential current (i) induced instantaneously, (ii) delayed at regular intervals, or (iii) induced similar to nerve spikes in a neuronal axon. The excitation of the reaction function corresponds to the excitation of physiologically diverse ion channels. As compared to actual experimental data, a combination of (iii) scenarios is known to be the most accurate. However, the excitation of the reaction function delayed at regular intervals (ii) will be mainly described to simplify the description below. A delay time $T_0$ may vary according to each model.

The ETM $\mathcal{T}$ denotes the time when the excitation or event starts at the corresponding point. When a sequence of events progresses through all domains, a sequence of excitations is seen as a wave.

FIG. 1 illustrates an example of a gradient of an ETM. The magnitude $\nabla \mathcal{T}$ of a gradient of an ETM between $(\mathcal{T}_1, x_1)$ and $(\mathcal{T}_2, x_2)$ is as shown in the following expression.

$$\|\nabla \mathcal{T}\| \approx \frac{\mathcal{T}_2 - \mathcal{T}_1}{\|x_2 - x_1\|}$$

It can be seen that, when an ion molecule (ions) is positioned at a point $x_1$ at a time $\mathcal{T}_1$, the ion molecule moves along the gradient of the ETM and reaches a point $x_2$ within a short period of time. Therefore, a direction of a velocity is the same as a direction $\nabla \mathcal{T}$ of the gradient of the ETM. However, the magnitude of the velocity is equal to the inverse of the magnitude of the ETM, as shown in the following expression.

$$\|v\| \approx \frac{\|x_2 - x_1\|}{\mathcal{T}_2 - \mathcal{T}_1}$$

Therefore, a velocity vector may be derived as shown in Equation 7 below.

$$v = \frac{\nabla \mathcal{T}}{\|\nabla \mathcal{T}\|^2} \qquad \text{[Equation 7]}$$

The velocity vector is used to find a specific potential that changes the speed of propagation. Here, finding the specific potential is the same as finding an acceleration field in which a pattern of the propagated wave is changed from an initial stationary wave to be propagated.

An acceleration field a known as a convective acceleration in fluid dynamics, results from a temporal change of the velocity vector and the geometric deformation of a velocity vector distribution. The acceleration field a may be expressed as Equation 8 below.

$$a = \left( \frac{\partial}{\partial t} + (v \cdot \nabla) \right) v \qquad \text{[Equation 8]}$$

In particular, the acceleration field in a static velocity field is the same as the convective acceleration. Further, the convective acceleration is expressed as the sum of Lamb vectors, as shown in Equation 9 below.

$$\ell = (\nabla \times v) \times v \qquad \text{[Equation 9]}$$

The kinetic energy of the propagated wave is shown in Equation 10 below.

$$v \cdot \nabla v = \ell + \nabla \left( \frac{\|v\|^2}{2} \right) \qquad \text{[Equation 10]}$$

When a velocity vector is a gradient of a scalar map, the Lamb vector $\ell$ is zero. Consequently, the convective acceleration is equal to the kinetic energy of the propagated wave. Therefore, Equation 8 may be expressed as Equation 11 below.

$$a = \frac{\partial}{\partial t} + \ell + \nabla \left( \frac{\|v\|^2}{2} \right) \qquad \text{[Equation 11]}$$

It is assumed that the divergence of the velocity vector remains unchanged. A potential U is introduced, as shown in Equation 12 below.

$$\nabla \cdot \ell = -\nabla^2 U \qquad \text{[Equation 12]}$$

In fluid dynamics, the divergence of the Lamb vector corresponds to a flow of energy passing through the boundary. Further, the divergence of the Lamb vector may be interpreted as a ratio between a pressure p and a density $\rho$ as $p/\rho$ in the Bernoulli function. The divergence of the Lamb vector may be interpreted as an ion concentration that induces electrical diffusion in cardiac electrical propagation.

When $\nabla \cdot \ell$ has a positive value, the ion concentration increases in a corresponding region. That is, U increases. When $\nabla \cdot \ell$ has a negative value, the ion concentration decreases in a corresponding region. That is, U decreases.

It is assumed that the divergence of the velocity vector is constant. When the corresponding divergence is applied to Equation 11, Equation 12 may be expressed as Equation 13 below.

$$\nabla \cdot a = \nabla^2 \left( -U + \frac{\|v\|^2}{2} \right) \qquad \text{[Equation 13]}$$

The researcher constructed a model and verified the above-described time map method. Equations 1 and 2 are implemented in the context of a finite difference method on a one-dimensional straight line. A second-order differentiation technique is used for the Laplace operator with Neumann boundaries at both ends. For time marching, a fourth-order specified Runge-Kutta scheme with sufficiently small dt compared to dx is used.

The researcher uses two types of two-variable models. One is a modified FitzHugh-Nagumo (FHN) model, and the other is an Aliev-Panfilov (AP) model.

Figure 2:
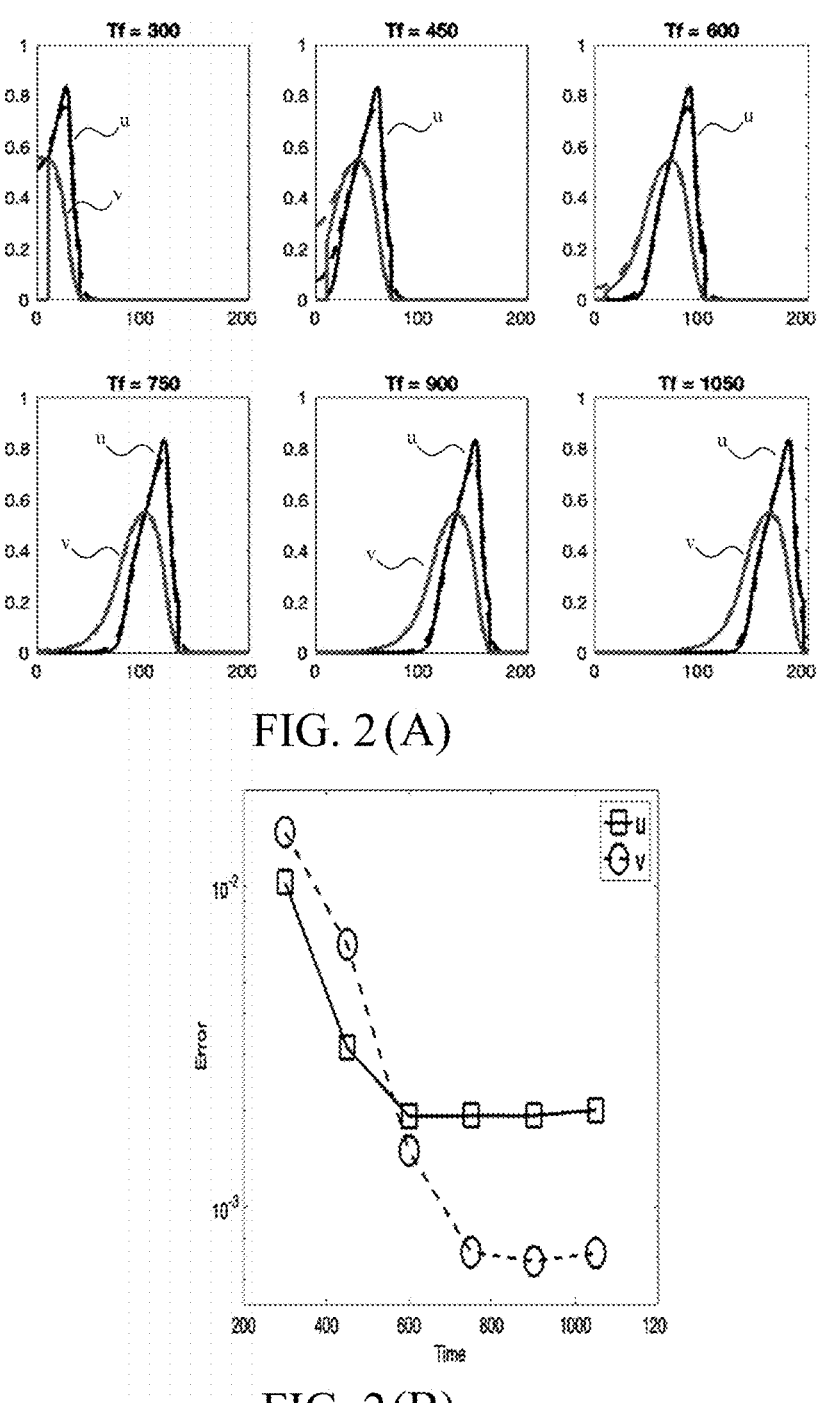
FIGS. 2(A) and 2(B) show the results of comparing solutions of an excitation time map and a partial differential equation in a FitzHugh-Nagumo (FHN) model.

FIGS. 2(A) and 2(B) show the results of comparing solutions of an ETM and a partial differential equation in an FHN model. In FIGS. 2(A) and 2(B), a dashed line represents the solution of the partial differential equation, and a solid line represents the solution of the ETM. In the FHN model, 0.2 is used as $I_{app}$ for the ETM. 25.0 is used as a delay time $T_0$. Time marching of abase time map is mostly independent of dx. However, the researcher uses $\Delta t=0.01$ for the ETM method when $\Delta t=0.001$ is used for a mathematical solution of the partial differential equation in Equation 1. FIG. 2(A) shows a simulation result of cardiac electrical propagation. u denotes a membrane potential, and v denotes a time vector. Referring to FIG. 2(A), the dashed line (solution of the partial differential equation) almost overlaps the solid line (the result of the ETM). Therefore, it can be seen that the solution of the partial differential equation is almost the same as the result of the ETM. FIG. 2(B) shows errors between the partial differential equation and the ETM. The errors in the two methods are in average 0.02 for u and 0.008 for respectively.

Figures 3A, 3B:
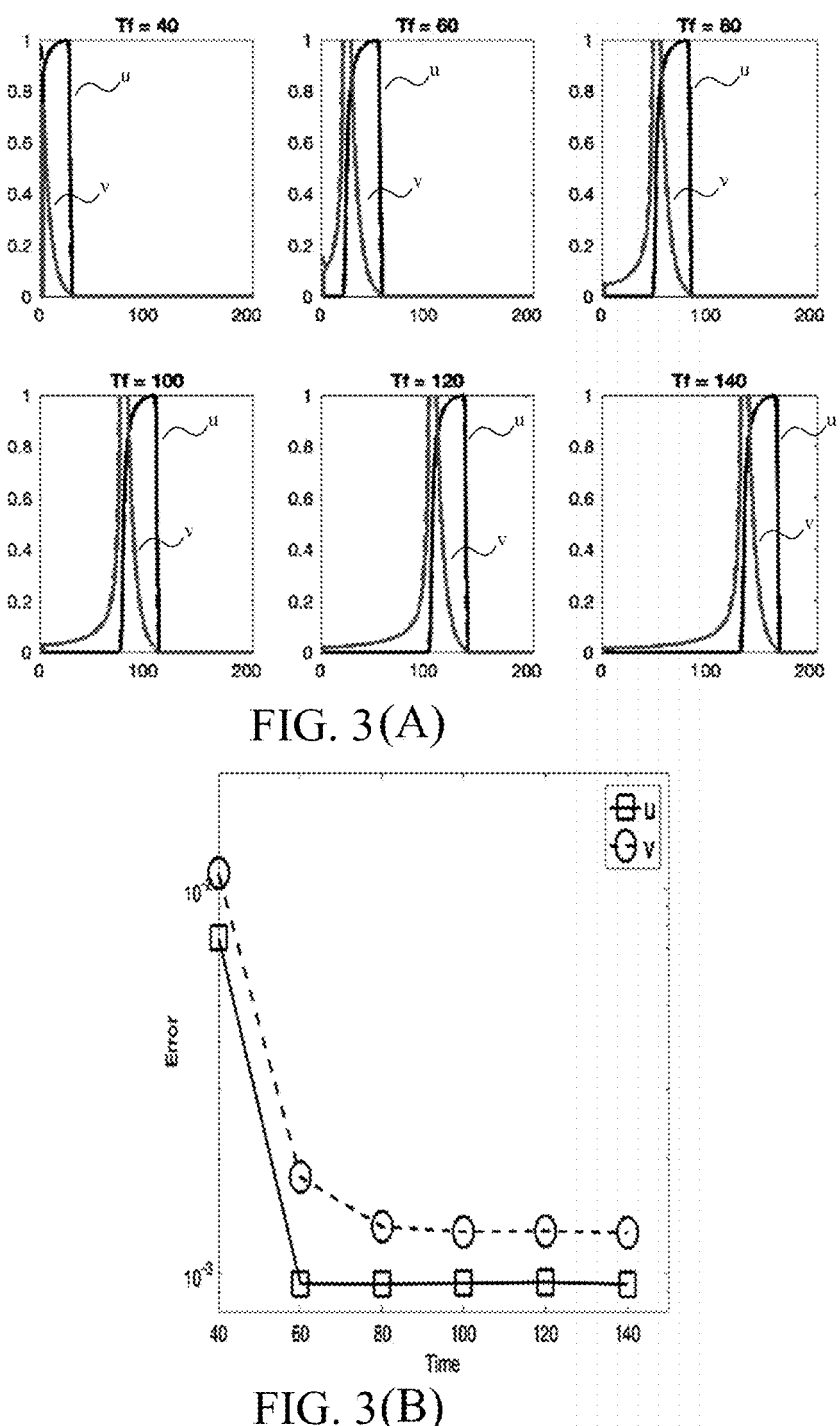
FIGS. 3(A) and 3(B) show the results of comparing solutions of an excitation time map and a partial differential equation in an Aliev-Panfilov (AP) model.

FIGS. 3(A) and 3(B) show the results of comparing solutions of an ETM and a partial differential equation in an AP model. In FIGS. 3(A) and 3(B), a dashed line represents the solution of the partial differential equation, and a solid line represents the solution of the ETM. In the AP model, 0.2 is used as $I_{app}$ for the ETM. 1.0 is used as a delay time $T_0$. The researcher uses $\Delta t=0.01$ for the ETM method when $\Delta t=0.001$ is used for a mathematical solution of the partial differential equation in Equation 1. FIG. 3(A) shows a simulation result of cardiac electrical propagation. u denotes a membrane potential, and v denotes a time vector. Referring to FIG. 3(A), the dashed line (solution of the partial differential equation) almost overlaps the solid line (the result of the ETM). Therefore, it can be seen that the solution of the partial differential equation is almost the same as the result of the ETM. FIG. 3(B) shows errors between the partial differential equation and the ETM. The errors in the two methods are in average 0.015 for u and 0.014 for v.

Figures 4A, 4B:
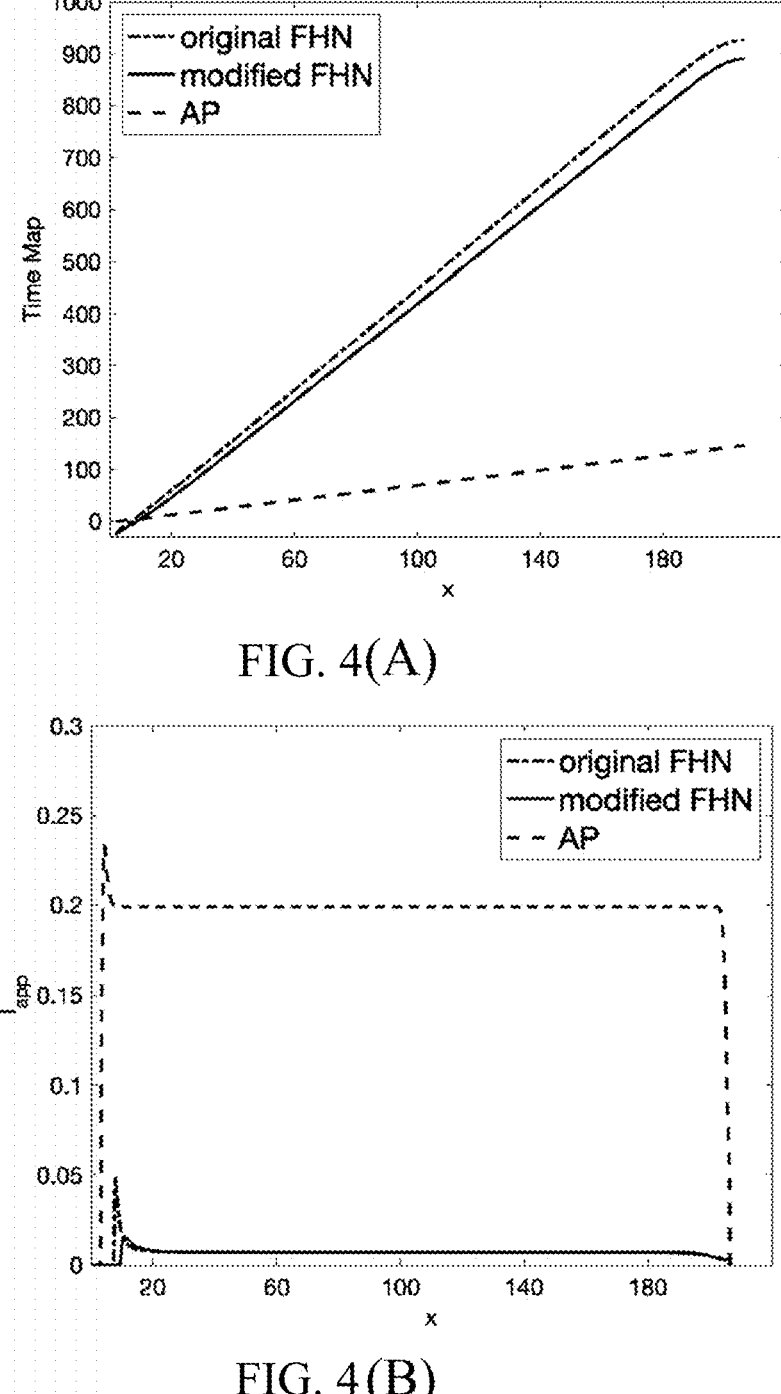
FIGS. 4(A) and 4(B) show excitation time maps and magnitudes of diffusion of excitation times in a researcher's verification experiment.

FIGS. 4(A) and 4(B) show ETMs and magnitudes of diffusion of excitation times in the researcher's verification experiment.

FIG. 4(A) shows a one-dimensional ETM. The ETM may be calculated by Equation 3. Further, $I_{app}$ may be measured as the magnitude of the Laplace operator in the corresponding ETM. In FIG. 4(A), the ETM is expressed as a straight line because a conduction velocity of an action potential may be calculated as a gradient of the ETM as shown in Equation 14 below.

$$\text{Conduction velocity} = \left(\frac{d\,\{ETM\}}{dx}\right)^{-1} = \frac{dx}{d\,\{ETM\}} \qquad \text{[Equation 14]}$$

FIG. 4(B) shows an actual $I_{app}$ transferred from neighboring cells due to diffusion. In an AP model, the magnitude of diffusion in an ETM is similar to the value of $I_{app}$ in the ETM. However, in a modified FHN model, the magnitude of diffusion is 0.02, which is somewhat smaller than the magnitude 0.2 of $I_{app}$ in an ETM.

Figures 5A, 5B:
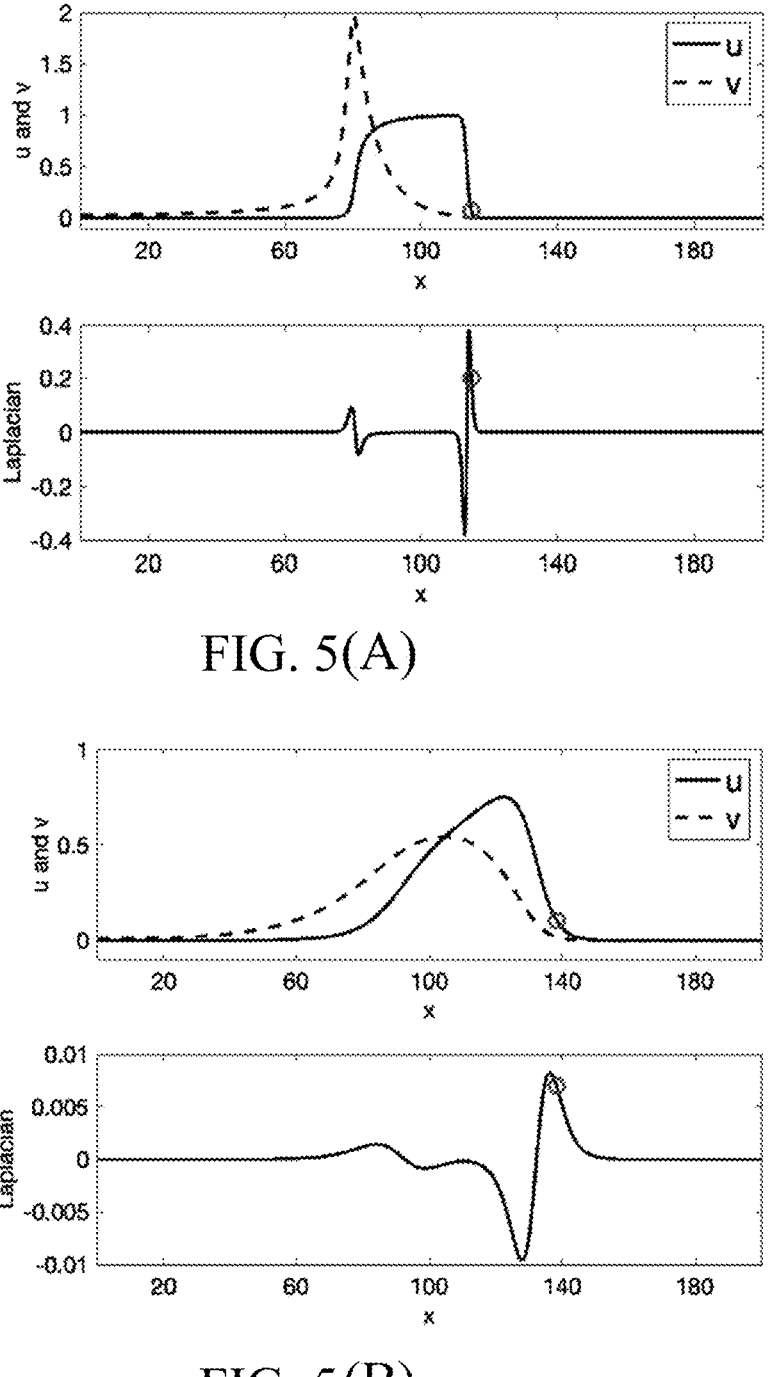
FIGS. 5(A) and 5(B) show positions of excitation time maps in an AP model and an FHN model.

FIGS. 5(A) and 5(B) show the positions of ETMs in an AP and FHN model. The ETMs may be used to determine the magnitude of $I_{app}$ based on diffusion and errors relative to $I_{app}$. A solution of a partial differential equation is derived with values of $\Delta t=1.0e-3$ and h=0.1. h denotes a distance that constantly increases or decreases in the finite difference method. The ETMs are used with $\Delta t=0.01$ and $I_{app}=0.2$. The errors are measured at T=600 for the FHN model and measured at T=80 for the AP model. In FIG. 5(A), a wavefront of the action potential increases sharply in the AP model. The magnitude of $I_{app}$ requested in the ETM is approximately equal to the magnitude of diffusion. However, in FIG. 5(B), a wavefront of the action potential increases slowly in the modified FHN model. Therefore, in the FHN model, diffusion is not instantaneous but changes slowly. Therefore, the magnitude of $I_{app}$ requested in the ETM should have more significant value than diffusion. The magnitude of $I_{app}$ may be a value obtained by integrating the magnitude of diffusion up to the excitation time.

Figure 6:
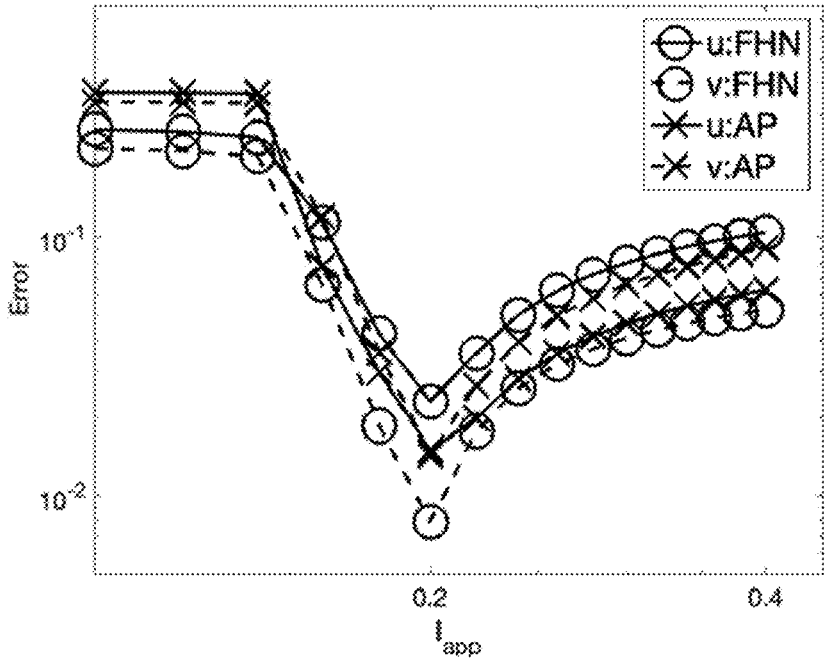
FIGS. 6(A) and 6(B) show errors versus input current ($I_{app}$) in an AP model and an FHN model.
Figure 6:
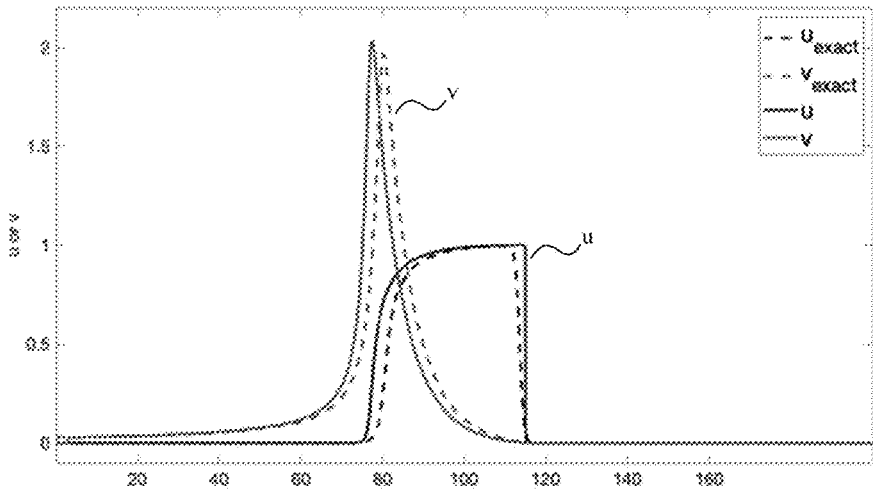

FIGS. 6(A) and 6(B) show errors relative to $I_{app}$ in an AP and FHN model.

FIG. 6(A) shows errors relative to $I_{app}$ in the verification experiment described above. $\Delta t$ for the partial differential equation is set to 0.001, and $\Delta t$ for the ETM is set to 0.01. Domains are x=[0, 516*4] and $\Delta x=0.1$. Referring to FIG. 6(A), it can be seen that accuracy of the ETM is determined by the magnitude of $I_{app}$. In both models, $I_{app}=0.2$ shows the most accurate value. When $I_{app}$ has a small value, such as $I_{app}<1.6$, an external input has a value lower than a threshold value, and excitation does not occur in each cell.

FIG. 6(B) shows an action potential duration for a considerable value of $I_{app}$. In FIG. 6(B), $I_{app}=1.0$ is used. When $I_{app}$ is greater than an optimal value, the action potential duration is longer than the correct section. The maximum magnitude of the action potential does not change with increasing $I_{app}$. In contrast a wave back of the action potential is further delayed when a position of the wavefront advances somewhat. A width of a second variable v does not change significantly, but a phase error of v occurs. Therefore, unlike the solution of the partial differential equation, the calculation of $I_{app}$ is important for the accuracy of the ETM method.

Even when $I_{app}$ is implemented with real-world data, the technique using the ETM allows computation time to be reduced.

In the solution of the partial differential equation of Equation 1, a time step size is limited according to $\Delta x$ in the Laplacian solution operation. For example, when $\Delta x=0.1$, $\Delta t$ for a second-order finite difference method of the Laplace operator cannot have a value larger than 0.001. However, in the ETM, the time step size is not limited. Table 1 below shows the results of comparing CPU times and errors of the partial differential equation method and the ETM method at $I_{app}=0.2$. The errors are measured at T=600 for the FHN model and measured at T=100.0 for the AP model.

TABLE 1

| dt | 1.0e−3 | 1.0e−3 | 0.01 | 0.02 | 0.1 | 0.2 |
|---|---|---|---|---|---|---|
| FHN CPU time (%) | 64.32 | 32.45 | 6.48 | 3.23 | 0.65 | 0.33 |
| Error (u) | 0.027 | 0.027 | 0.027 | 0.027 | 0.027 | 0.027 |
| Error (v) | 0.017 | 0.017 | 0.017 | 0.017 | 0.019 | 0.023 |
| AP CPU time (%) | 65.89 | 32.58 | 6.54 | 3.28 | 0.65 | 0.33 |
| Error (u) | 0.017 | 0.017 | 0.017 | 0.017 | 0.019 | 0.023 |
| Error (v) | 0.016 | 0.016 | 0.016 | 0.017 | 0.018 | 0.021 |

In the ETM method, $\Delta t$ may increase to 0.1 without significantly degrading accuracy. When $\Delta t=0.1$, the CPU time for the ETM is less than 1% of that of the partial differential equation method. Therefore, it can be said that the ETM method may be sufficiently used in real-time medical simulation using data with real noise. It can be seen that when $\Delta x$ decreases, the ETM method has a result similar to that of the partial differential equation method within an accuracy range of 1.0e-2, although the CPU time slightly decreases. In the ETM method, the errors are not significantly reduced even when $\Delta x$ becomes smaller.

Table 2 below shows the results of comparing CPU times and errors of the partial differential equation method and the ETM method at $I_{app}=0.2$ by applying different mesh sizes. The errors are at T=600 for the FHN model and measured at T=100.0 for the AP model.

TABLE 2

| h | 2e−2 | 1e−2 | 5e−3 | 2.5e−3 |
|---|---|---|---|---|
| dt | 4e−3 | 1e−3 | 2.5e−4 | 6.25e−5 |
| FHN CPU time (%) | 24.73 | 6.48 | 1.33 | 0.32 |
| Error (u) | 0.027 | 0.027 | 0.027 | 0.027 |
| Error (v) | 0.014 | 0.014 | 0.014 | 0.015 |
| AP CPU time (%) | 25.49 | 6.54 | 1.40 | 0.34 |
| Error (u) | 0.017 | 0.017 | 0.017 | 0.017 |
| Error (v) | 0.017 | 0.016 | 0.016 | 0.016 |

Unlike the partial differential equation method, in the ETM method, the total CPU time does not change significantly with the change in mesh size. That is, the ETM method may derive a solution in realtime, even for a very fine mesh.

The researcher performed verification on a one-dimensional ETM. However, the above-described technique also applies to ETMs in a secondary planar form and ETMs in a three-dimensional form.

Figure 7:
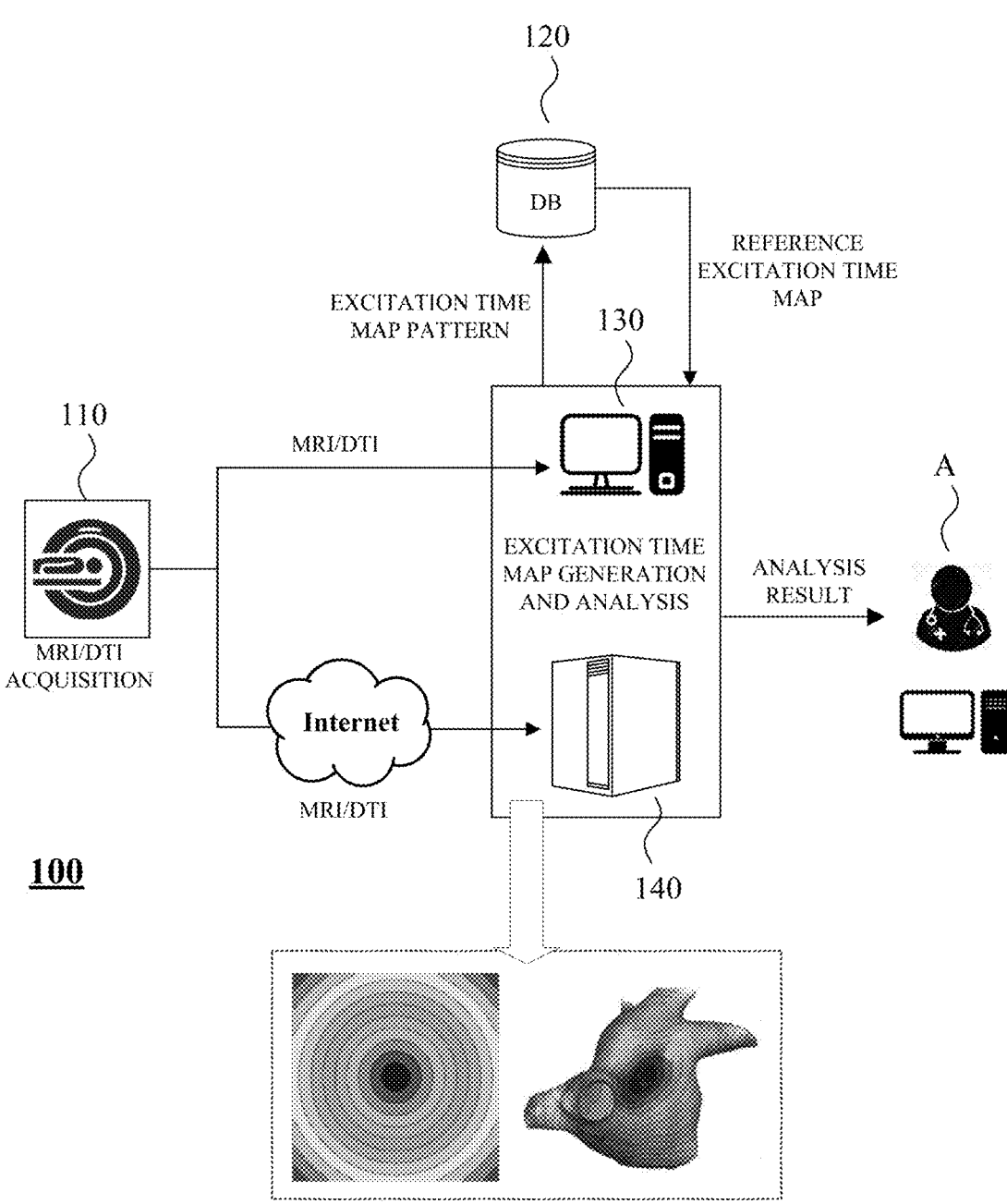
FIG. 7 illustrates an example of a system for evaluating a subject using an excitation time map.

FIG. 7 illustrates an example of a system 100 for evaluating a subject using an ETM. A device that generates an ETM on the basis of medical images of the subject to evaluate the subject is referred to as an analysis device. The analysis device may take the form of a computer device such as a personal computer (PC), a smart device, a network server, a data processing dedicated chipset, or the like. FIG. 7 illustrates an example in which the analysis device is a computer terminal 130 and a server 140.

Medical image equipment 110 generates medical images (e.g., magnetic resonance imaging (MRI) images or diffusion tensor imaging (DTI) images) of the subject. The medical image equipment 110 obtains medical images including parts of the subject's brain, heart, and the like. The medical image equipment 110 generates medical images (time-series medical images) of the subject for a certain period of time.

User A may analyze the medical images using the computer terminal 130. The computer terminal 130 may receive medical images of a specific subject from the medical image equipment 110 through a wired or wireless network. In some cases, the computer terminal 130 may be a device physically connected to the medical image equipment 110.

The computer terminal 130 may generate an ETM using the medical images. The computer terminal 130 may generate an ETM by obtaining a solution of an ODE with cell having a membrane potential as a variable as shown in Equation 2. The computer terminal 130 generates a scalar map (ETM) representing excitation times at grid points of all domains using Equation 3. Here, the domains may be a two- or three-dimensional medical image for a certain period of time. The grid points of the domains may correspond to points or cells of a specific tissue. Further, the computer terminal 130 may generate an ETM using an equation such as Equation 4 or 6. The computer terminal 130 may generate a one-dimensional ETM or a multidimensional ETM. The one-dimensional ETM is shown in FIG. 4(A). The two- or three-dimensional ETM is shown at the bottom of FIG. 7.

The computer terminal 130 may interpret the ETM itself for the subject as specific information or a pattern of the corresponding subject. Furthermore, the computer terminal 130 may calculate membrane potentials and/or velocity vectors for a specific point or a plurality of points extracted from the ETM as the specific information of the corresponding subject.

The computer terminal 130 may store the ETM and/or the information extracted from the ETM in a database (DB) 120. The computer terminal 130 may store an ETM for a population in the DB 120. An ETM for a population having a specific phenotype may be stored in the DB 120. The specific phenotype may be a particular condition or disease. An ETM for a normal group and an ETM for an abnormal group (patients with a specific disease) according to the phenotype may be stored in the DB 120.

The computer terminal 130 may compare the ETM (or information extracted from the ETM) for the subject, which is a target currently being analyzed, with the ETM for a reference group (normal or abnormal). In this case, the ETM may be referred to as a reference ETM. Accordingly, the computer terminal 130 may calculate an analysis result for the subject's condition or disease. User A may check the analysis result through the computer terminal 130.

The server 140 may generate an ETM using the medical images. The server 140 may generate an ETM by obtaining a solution of an ODE having a membrane potential of a cell as a variable as shown in Equation 2. The server 140 generates a scalar map (ETM) representing excitation times at grid points of all domains using Equation 3. Here, the domains may be a two- or three-dimensional medical image for a certain period of time. The grid points of the domains may correspond to points or cells of a specific tissue. Further, the server 140 may generate an ETM using an equation such as Equation 4 or 6. The server 140 may generate a one-dimensional ETM or a multidimensional ETM. The one-dimensional ETM is as shown in FIG. 4(A). The two- or three-dimensional ETM is as shown at the bottom of FIG. 7.

The server 140 may interpret the ETM itself for the subject as specific information or a pattern of the corresponding subject. Furthermore, the server 140 may calculate membrane potentials and/or velocity vectors for a specific point or a plurality of points extracted from the ETM as the specific information of the corresponding subject.

The server 140 may store the ETM and/or the information extracted from the ETM in the DB 120. The server 140 may store an ETM for a population in the DB 120. The ETM for a population having a specific phenotype may be stored in the DB 120. The server 140 may compare the ETM (or information extracted from the ETM) for the subject, which is a target currently being analyzed, with the ETM for a reference group (normal or abnormal). Accordingly, the server 140 may calculate an analysis result for the subject's condition or disease. The server 140 may transmit a result of analyzing the medical images to a user terminal of user A. User A may check the analysis result through the user terminal.

Figure 8:
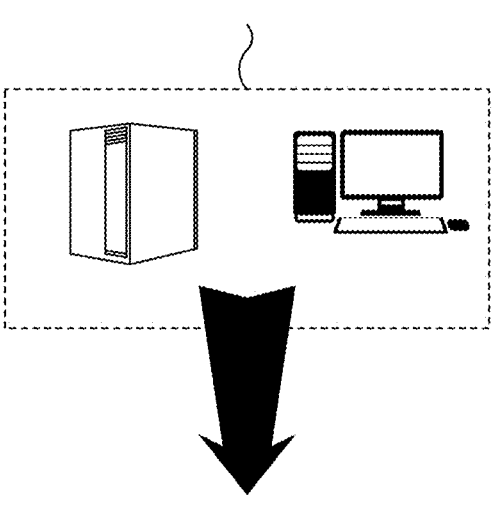
FIG. 8 illustrates an example of an analysis device for analyzing biological signals using an excitation time map.

FIG. 8 illustrates an example of an analysis device 200 for analyzing biological signals using an ETM. The analysis device 200 corresponds to the analysis device 130 or 140 described above (in FIG. 7). The analysis device 200 may be physically implemented in various forms. For example, the analysis device 200 may take the form of a computer device such as a PC, a smart device, a network server, a data processing dedicated chipset, or the like.

The analysis device 200 may include a storage device 210, a memory 220, a computing device 230, an interface device 240, a communication device 250, and an output device 260.

Medical images (MRI images, DTI images, etc.) of a subject generated by medical image equipment may be stored in the storage device 210.

An ETM for a population may be stored in the storage device 210 like the DB 120.

Code or a program for calculating the ETM on the basis of the medical images may be stored in the storage device 210.

The memory 220 may store data, information, and the like generated during a process in which the analysis device 200 calculates the ETM on the basis of the medical images.

The interface device 240 is a device that receives a certain command and data from an external object. The interface device 240 may receive the medical images of the subject from a physically connected input device or an external storage device. The interface device 240 may receive an ETM for a population (normal group and/or abnormal group) from the physically connected input device or the external storage device. The interface device 240 may transmit the ETM calculated based on the medical images to the external object. The interface device 240 may transmit an evaluation result of a specific subject's condition or disease to the external object.

The communication device 250 is a component that receives or transmits certain information through a wired or wireless network. The communication device 250 may receive the medical images of the subject from the external object. The communication device 250 may receive the ETM for the population (normal group and/or abnormal group) from the external object. The communication device 250 may transmit a dementia-related index calculated based on the medical images to the external object such as the user terminal. The communication device 250 may transmit the evaluation result of the specific subject's condition or disease to the external object.

Furthermore, the interface device 240 may be a component that receives the medical images or data received by the communication device 250.

The output device 260 is a device that outputs certain information. The output device 260 may output an interface necessary for a data processing process, the medical images, the ETM, information extracted from the ETM, the evaluation result of the subject, and the like.

The computing device 230 may generate an ETM using the medical images.

The computing device 230 may generate an ETM by obtaining a solution of an ODE having a membrane potential of a cell as a variable as shown in Equation 2.

The computing device 230 generates a scalar map (ETM) representing excitation times at grid points of all domains using Equation 3.

The computing device 230 may generate an ETM using an equation such as Equation 4 or 6.

The computing device 230 may generate a one-dimensional ETM or a multidimensional ETM.

The computing device 230 may interpret the ETM itself for the subject as specific information or a pattern of the corresponding subject.

The computing device 230 may calculate membrane potentials and/or velocity vectors for a specific point or a plurality of points extracted from the ETM as the specific information of the corresponding subject.

The computing device 230 may compare the ETM for the subject with the ETM for the reference group (normal or abnormal). The ETM for the reference group may be stored in the storage device 210 or the external object.

The computing device 230 may determine that the subject is normal when the ETM for the subject or the information extracted from the ETM is similar to that of the normal group. Alternatively, the computing device 230 may determine that the subject is abnormal when the ETM for the subject or the information extracted from the ETM is similar to that of the abnormal group. Here, the abnormal group may include a patient with a specific disease, a candidate group for a specific disease, and a patient with a prognosis after a specific surgery.

As described above, the ETM may take the form of a one-dimensional vector, a two-dimensional image, a three-dimensional image, or the like. The computing device 230 may use a pre-built learning model to evaluate the subject's condition or whether the subject has a disease. The corresponding learning model may be a machine learning model such as a deep learning model. The learning model may be pre-trained using input data (ETM) and correct answer values (population's condition or disease belonging to learning data).

The computing device 230 may be a device such as a processor that processes data and performs certain arithmetic operations, an application processor (AP), or a chip in which program is embedded.

Further, the method of generating the ETM and the method of evaluating the subject based on the ETM described above may be implemented as program (or application) including an executable algorithm that can be executed on a computer. The program may be stored and provided in a non-transitory computer readable medium.

The non-transitory computer readable medium is not a medium that stores data for a short moment, such as a register, a cache, a memory, or the like, but is a medium that stores data semi-permanently and can be read by a device. Specifically, various applications or programs described above may be stored and provided in a non-transitory computer readable medium such as a compact disc (CD), a digital video disc (DVD), a hard disk, a Blu-ray disc, a Universal Serial Bus (USB), a memory card, a read-only memory (ROM), a programmable ROM (PROM), an erasable PROM (EPROM), an electrically EPROM (EEPROM), a flash memory, or the like.

A transitory computer readable medium includes various random-access memories (RAMs) such as a static RAM (SRAM), a dynamic RAM (DRAM), a synchronous DRAM (SDRAM), a double data rate SDRAM (DDR SDRAM), an enhanced SDRAM (ESDRAM), a synchronous-link DRAM (SLDRAM), and a direct Rambus RAM (DRRAM).

Embodiments and the accompanying drawings only clearly show a part of the technical idea included in the above-described technique, and it will be apparent that all modifications and specific embodiments that can be easily construed by those skilled in the art within the scope of the technical idea included in the specification and drawings of the above-described technique are included in the scope of the above-described technique.

What is claimed is:

1. An analysis device for generating an excitation time map, comprising:
an interface device configured to receive time-series medical images of a subject; and
a computing device configured to generate an excitation time map by solving a diffusion reaction of electrical signals calculated from the time-series medical images using a solution of an ordinary differential equation,
wherein the ordinary differential equation comprises (i) a function of the time of maximum membrane potential and (ii) a reaction function for a membrane potential and ion channels, and
wherein the excitation time map is a scalar map including excitation times at all grid points of the time-series medical images,
wherein the excitation time at each grid point is directly determined as a cell-specific time at which the membrane potential at the grid point reaches a maximum value, and
wherein the excitation time map is generated based on the determined excitation times determined independently for each grid point.

2. The analysis device of claim 1, wherein the time-series medical images include magnetic resonance imaging (MRI) or diffusion tensor imaging (DTI) images.

3. The analysis device of claim 1, wherein the computing device generates the excitation time map using the following expression, $$\mathcal{T}(x_i) = \frac{\sum_j t_j \|\nabla u(x_i, t_j)\|}{\sum_j \|\nabla u(x_i, t_j)\|} - T_0,$$

for all $$t = t_j \text{ satisfying } \frac{du}{dt} > 0,$$

(u denotes the membrane potential, $x_i$ denotes an $i^{th}$ grid point among the grid points, and $t_j$ denotes a time in the time-series medical image).

4. The analysis device of claim 1, wherein the ordinary differential equation is expressed as the following expression for cell B, $$\frac{du(x_B)}{dt} = I_{app} \delta_T^{T_B} + R(u(x_B), \ldots),$$

($x_B$ denotes cell B, R(u, . . . ) denotes the reaction function for the membrane potential u and the ion channels, $I_{app}$ denotes a magnitude of a current transmitted from the outside with respect to cell B, $T_B$ denotes a period of time for cell B to reach a maximum membrane potential, $$\delta_T^{T_B}$$

denotes a Kronecker delta function for T and $T_B$, and T denotes a specific time).

5. A method of evaluating a subject using an excitation time map, comprising:
receiving, by an analysis device, time-series medical images of a subject;
generating, by the analysis device, an excitation time map by solving a diffusion reaction of electrical signals calculated from the time-series medical images using a solution of an ordinary differential equation; and
comparing, by the analysis device, the excitation time map for the subject with a pre-built reference excitation time map and evaluating a condition of the subject,
wherein the ordinary differential equation comprises (i) a function of the time of maximum membrane potential and (ii) a reaction function for a membrane potential and ion channels, and
wherein the excitation time map is a scalar map including excitation times at all grid points of the time-series medical images,
wherein the excitation time at each grid point is directly determined as a cell-specific time at which the membrane potential at the grid point reaches a maximum value, and
wherein the excitation time map is generated based on the determined excitation times determined independently for each grid point.

6. The method of claim 5, wherein the time-series medical images include magnetic resonance imaging (MRI) or diffusion tensor imaging (DTI) images.

7. The method of claim 5, wherein the analysis device generates the excitation time map using the following expression, $$\mathcal{T}(x_i) = \frac{\sum_j t_j \|\nabla u(x_i, t_j)\|}{\sum_j \|\nabla u(x_i, t_j)\|} - T_0,$$

for all $$t = t_j \text{ satisfying } \frac{du}{dt} > 0,$$

(u denotes the membrane potential, $x_i$ denotes an $i^{th}$ grid point among the grid points, and $t_j$ denotes a time in the time-series medical image).

8. The method of claim 5, wherein the ordinary differential equation is expressed as the following expression for cell B, $$\frac{du(x_B)}{dt} = I_{app}\delta_T^{T_B} + R(u(x_B), \ldots),$$

($x_B$ denotes the cell B, R(u, . . . ) denotes the reaction function for the membrane potential u and the ion channels, Lapp denotes a magnitude of a current transmitted from the outside with respect to cell B, $T_B$ denotes a period of time for cell B to reach a maximum membrane potential, $$\delta_T^{T_B}$$

denotes a Kronecker delta function for T and $T_B$, and T denotes a specific time).

\*   \*   \*   \*   \*